United States Patent
Blume et al.

(10) Patent No.: US 6,946,466 B2
(45) Date of Patent: Sep. 20, 2005

(54) AROMATIC SULFONAMIDES AS PEROXYNITRITE-REARRANGEMENT CATALYSTS

(75) Inventors: Thorsten Blume, Schildow (DE); Roland Neuhaus, Berlin (DE); Detlev Suelzle, Berlin (DE); Iris Pribilla, Villeneuve (FR); Gisbert Depke, Berlin (DE); Joseph S. Beckman, Corvallis, OR (US)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/410,594

(22) Filed: Apr. 10, 2003

(65) Prior Publication Data

US 2004/0204452 A1 Oct. 14, 2004

(51) Int. Cl.[7] .................. C07D 401/02; A61K 31/47
(52) U.S. Cl. .................. 514/252.19; 514/307; 514/314; 514/326; 514/380; 514/445; 546/139; 546/152; 546/207; 548/243; 549/59; 544/359
(58) Field of Search .................. 514/252.19, 307, 514/314, 326, 380, 445, 317; 544/359; 546/139, 152, 207, 192; 548/243; 549/59

(56) References Cited

FOREIGN PATENT DOCUMENTS

| WO | WO 9531197 | 11/1995 | | |
|----|------------|---------|---|---|
| WO | WO 9805315 | 2/1998 | | |
| WO | WO98/270081 A1 | * 6/1998 | ......... | C07D/333/34 |
| WO | WO 0126655 | 4/2001 | | |

OTHER PUBLICATIONS

Dhanoa et al, Med. Chem. Res. vol. 8 No. 4–5, pp. 187–205, 1998.*
Database Chemabs Online!, Obafemi, Craig A., "Studies in the heterocyclic compounds V. some reactions of 5–chloro–2–thiophenesulfonyl derivatives," XP002295243, retrieved from STN, Database accession No. 97:162734, RN 83222–35–9, abstract, Chemical Abstracts Service, Columbus, Ohio; & Phosphorus and Sulfur and the related elements, 13(1), 119–31 CODEN: PREEDF; ISSN: 0308–664X, 1982.
Database Chemabs Online! Zani, F. et al., "Antimicrobial and genotoxic properties of quinoline derivatives," XP002295244, retrieved from STN, Database accession No. 121:245157, RN 158729–26–1, abstract, Chemical Abstracts Service, Columbus, Ohio; & Bollettino Chimico Farmacuetico 133(5), 328–38 CODEN: BCFAAI; ISSN: 0006–6648, 1994.

Database Beilstein, Beilstein Institute for Organic Chemistry, Frankfurt–Main, DE, XP002295245, Database accession No. BRN 9276608, abstract; & J Org Chem, vol. 68, No. 1, 2003, pp. 115–119.

Database Beilstein, Beilstein Institute for Organic Chemistry, Frankfurt–Main, DE; XP002295247, Database accession No. BRN 3380062, abstract & Chem Ber, vol. 88, 1995, pp. 1485–1491.

Database Beilstein, Beilstein Institute for Organic Chemistry, Frankfurt–Main, DE; XP002295248, Database accession No. BRN 2740715, abstract. & J. Amer Chem Soc, 1952, pp. 2597–2599, vol. 74.

Database Beilstein, Beilstein Institute for Organic Chemistry, Frankfurt–Main, DE; XP002295249, Database accession No. BRN 2747420, Abstract & J Organomet Chem, vol. 71, 1974, pp. 347–365.

Database Beilstein, Beilstein Institute for Organic Chemistry, Frankfurt–Main, DE; XP002295250, Database accession No. 2988361 abstract & J Gen Chem USSR, vol. 19, 1949, p. 683.

Database Chemcats, Chemical Abstracts Service, Columbus, OH;XP002295251, Order Nos.; BAS 1124290, 4049–0074 & Jul. 9, 2002, Interchim Intermediates, Montlucon, Cedex, FR.

* cited by examiner

Primary Examiner—Zinna Northington Davis
(74) Attorney, Agent, or Firm—Millen, White, Zelano & Branigan, P.C.

(57) ABSTRACT

The invention relates to the use of aromatics sulfonamides of the general formula I as peroxynitrite rearrangement catalysts, to the preparation thereof and to the use thereof as medicament for the treatment of various disorders.

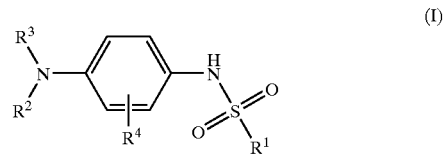

(I)

23 Claims, 1 Drawing Sheet

Fig.: 1
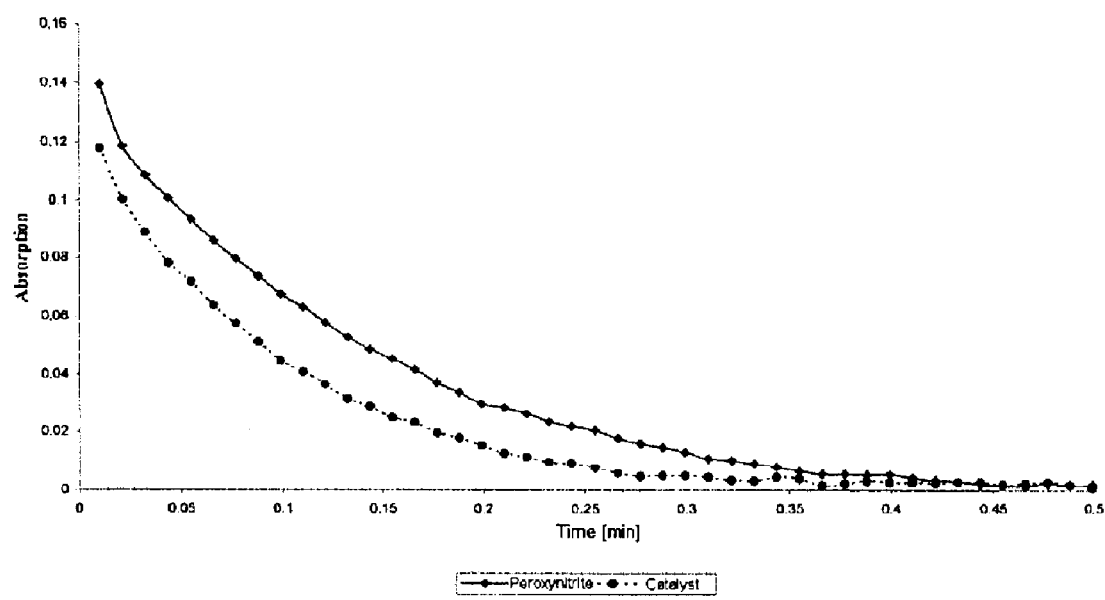

AROMATIC SULFONAMIDES AS PEROXYNITRITE-REARRANGEMENT CATALYSTS

The present invention relates to sulfonamides as peroxynitrite-rearrangement catalysts, to the preparation thereof and to the use thereof for producing medicaments for treating various disorders.

Peroxynitrite was already described by Beckman et al. (Beckman et al., 1990, Proc. Natl. Acad. Sci. USA. 87, 1620–1624) as a toxic metabolite resulting from the diffusion-controlled reaction between nitric oxide (NO) and superoxide anion ($O_2^-$). Peroxynitrite is involved in a number of inflammatory processes which play an important part in disorders such as, for example, Alzheimer's dementia, multiple sclerosis, amyotrophic lateral sclerosis, and are thought to be responsible for cell death and the induction of apoptosis.

Peroxynitrite reacts with a large number of proteins by oxidizing or nitrating amino acid residues. Nitrotyrosine residues are found to be increased in the tissue of patients suffering from multiple sclerosis, because peroxynitrite causes nitration of the tyrosine residues of the filaments of the motor neurons. The contraction of the filaments which is impaired in this way results in neuronal dysfunction (Estévez et al., 1999, Science 286, 2498–2500). One reason for the impaired vasoconstriction after a stroke is the peroxynitrite-induced oxidation of the lipid residues in the cell membrane, leading to endothelial injuries and, resulting therefrom, the formation of edema and neutrophils.

A pharmacological intervention in order to prevent the peroxynitrite-mediated effects is possible at either the reactant (NO, and $O_2^-$) or the product (peroxynitrite).

One approach on the part of the product peroxynitrite was described first by Salvemini et al. (Salvemini et al., 1998, Proc. Natl. Acad. Sci. USA., 95, 2659–2663). In this approach, peroxynitrite is rearranged by means of a catalyst into harmless end products. It is possible with only low concentrations of catalyst to convert a large quantity of peroxynitrite. One advantage of this approach is that it cannot result in the formation of the disadvantageous decomposition products such as, for example, reactive oxygen species, and that the inhibition of superoxide dismutase (SOD) by peroxynitrite is abolished. Accordingly, the treatment method with novel compounds has a two-fold advantage in the treatment of disorders. Thus, on the one hand, the rate of conversion of peroxynitrite is increased up and, on the other hand, SOD is protected from inactivation by peroxynitrite.

Possible transformation catalysts disclosed to date are metal-containing complexes (WO 95/31197, U.S. Pat. No. 6,245,758, WO 98/04132, U.S. Pat. No. 5,872,124, WO 00/75144, WO 01/26655, U.S. Pat. No. 6,372,727). The metalloporphyrins described by Salvemini et al. show a protective effect in models of inflammation (Salvemini et al., 1998, Proc. Natl. Acad. Sci. USA. 95, 2659–2663 and British J. Pharmacol., 1999, 127, 685–692). The same class of compounds were described as effective in a bowel artery occlusion model by Cuzzocrea et al. (Cuzzocrea et al., 2000, FASEB J. 14 (9), 1061–1072 and Cuzzocrea et al., 2001, Pharmacology Rev. 53, 135–159). Cross et al. demonstrated the efficacy of this substance in an MS model ("experimental autoimmune encephalomyelitis" =EAE) in mice (Cross et al., 2000, J. Neuroimmunology 107, 21–28). Mackensen et al. showed for the first time the efficacy of a manganese-containing porphyrin in a focal ischemia model, the focal MCAO (middle cerebral artery occlusion) (Mackensen et al., 2001, J. Neurosci. 21, 4582–4592).

Little is known to date about the side effects such as toxicity, tolerability and in vivo availability, and the blood-brain barrier permeability of these known rearrangement catalysts.

Sulfonamides and analogs are already widely used and well characterized, for example, as dyes (U.S. Pat. No. 5,591,833) for photochemistry (JP 2001092091, JP 2001033922, EP 610653, JP 04346338) and as radio- or chemo-sensitizers (JP 09263581). They are, however, also described as active ingredients such as, for example, factor Xa inhibitors (U.S. Pat. No. 6,187,797, WO 99/32454, WO 98/57937, WO 98/57951, WO 98/28269, WO 97/38984, WO 97/23212), as modulators for the treatment of obesity and related disorders (WO 01/62737, WO 99/10320). Arylsulfonamides are described as CNS-active substances which achieve their effect through binding to the $5HT_6$ receptor (WO 98/27081). Substituted imidazoles show cytokine-inhibitory activity (U.S. Pat. No. 5,859,041) and WO 97/36580 describes substituted sulfonamides as protease inhibitors. Phenyl derivatives of sulfonamides are described in U.S. Pat. No. 6,083,987 as radical scavengers for the treatment and prevention of cerebral infarctions and cerebral edemas.

There is thus a great need for well tolerated, chemically stable and in vivo available substances (catalysts), in order in this way to increase the rearrangement of peroxynitrite into harmless products, for the treatment and prophylaxis of disorders caused by peroxynitrite-mediated reactions. These substances having in vivo activity can be used to develop medicaments for the treatment of disorders.

It has now been found that compounds of the general formula I

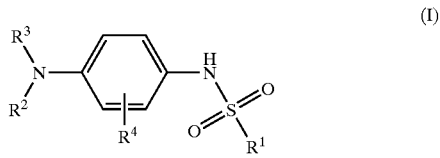

in which

R[1] is a $C_5$–$C_6$-cycloalkyl which may optionally be substituted one or more times by $C_1$–$C_6$-alkyl and whose ring may optionally be interrupted by one or more nitrogen, sulfur or oxygen atoms and/or may contain one or more possible double bonds in the ring, or is a $C_3$–$C_7$-aryl or $C_3$–$C_{12}$-heteroaryl, which may optionally be substituted one or more times, identically or differently, by halogen, hydroxyl, $C_1$–$C_6$-alkyl or $C_1$–$C_6$-alkoxy, R[2] and R[3] are each, independently of one another, $C_1$–$C_6$-alkyl or $C_1$–$C_6$-alkoxy, or R[2] and R[3] together with the nitrogen atom form a $C_5$–$C_6$-cycloalkyl ring which may optionally be interrupted by a further nitrogen atom in the ring, where the $C_5$–$C_6$-cycloalkyl ring may optionally be substituted by $C_1$–$C_4$-alkyl, and R[4] is hydrogen, hydroxyl, nitro, halogen, $C_1$–$C_6$-alkyl or the group COOH, $CF_3$ or $C_1$–$C_6$-alkoxy, and the isomers, diastereomers, enantiomers and salts thereof, overcome the known disadvantages, i.e. that the compounds of the invention having peroxynitrite-rearranging properties make targeted treatment possible for disorders caused by peroxynitrite.

Alkyl means in each case a straight-chain or branched alkyl radical such as, for example, methyl, ethyl, propyl, isopropyl, butyl, isobutyl, sec-butyl, tert-butyl, pentyl, isopentyl, hexyl, heptyl, octyl, nonyl and decyl.

Alkoxy means in each case a straight-chain or branched alkoxy radical such as, for example, methyloxy, ethyloxy, propyloxy, isopropyloxy, butyloxy, iso-butyloxy, sec-butyloxy, tert-butyloxy, pentyloxy, isopentyloxy or hexyloxy.

Cycloalkyl means in each case cyclopropyl, cyclobutyl, cyclopentyl, cyclohexyl and cycloheptyl.

Ring systems in which one or more possible double bonds may optionally be present in the ring mean, for example, cycloalkenyls such as cyclopropenyl, cyclo-butenyl, cyclopentenyl, cyclohexenyl, cycloheptenyl, where the linkage may take place either at the double bond or at the single bonds.

The aryl radical has in each case 6–12 carbon atoms, such as, for example, naphthyl, biphenylyl and, in particular, phenyl.

The heteroaryl radical comprises in each case 3–16 ring atoms and may contain in place of carbon one or more, identical or different, heteroatoms such as oxygen, nitrogen or sulfur in the ring, and may be mono-, bi- or tricyclic, and may in addition in each case be benzo-fused.

Examples which may be mentioned are:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc. and benzo derivatives thereof such as, for example, benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc. and benzo derivatives thereof such as, for example, quinolyl, isoquinolyl, etc.; or Azocinyl, indolizinyl, purinyl, etc. and benzo derivatives thereof; or quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, oxepinyl, etc.

If an acidic function is present, suitable salts are physiologically tolerated salts of organic and inorganic bases such as, for example, the readily soluble alkali metal and alkaline earth metal salts, and N-methylglucamine, dimethylglucamine, ethyl-glucamine, lysine, 1,6-hexanediamine, ethanolamine, glucosamine, sarcosine, serinol, trihydroxymethylamino-methane, aminopropanediol, Sovak base, 1-amino-2,3,4-butanetriol.

If a basic function is present, the physiologically tolerated salts of organic and inorganic acids are suitable, such as hydrochloric acid, sulfuric acid, phosphoric acid, citric acid, tartaric acid and others.

The provision of aromatic sulfonamides which act as peroxynitrite-rearrangement catalysts by the present invention solves the problem of the availability of well tolerated, chemically stable and in vivo active catalysts for developing medicaments for the treatment of disorders.

It is possible in the present invention to show by UV/VIS spectroscopy that the compounds of the invention catalyze the rearrangement of peroxynitrite to harmless end products, namely nitrate and nitrite. It can be shown by means of a model of cell damage that the compounds of the invention are protective and protect cells from peroxynitrite damage induced by the peroxynitrite donor SIN-1. It can likewise be shown that the compounds of the invention have no side effects, good solubility in water, chemical stability and a good in vivo availability and good brain penetration.

Particularly effective compounds of the general formula (I) are those in which $R^1$ is a $C_5$–$C_6$-cycloalkyl which may optionally be substituted one or more times by methyl, and whose ring may optionally be interrupted by one or more nitrogen, sulfur or oxygen atoms and/or one or more possible double bonds may be present in the ring, or is a $C_3$–$C_6$-aryl or $C_3$–$C_{12}$-heteroaryl, $R^2$ and $R^3$ are each, independently of one another, $C_1$–$C_6$-alkyl, or $R^2$ and $R^3$ together with the nitrogen atom form a $C_5$–$C_6$-cycloalkyl ring which may optionally be interrupted by a further nitrogen atom in the ring, where the $C_5$–$C_6$-cycloalkyl ring may optionally be substituted by $C_1$–$C_4$-alkyl, $R^4$ is hydrogen, or is the group $CF_3$, —O—$CH_3$ or nitro, and the isomers, diastereomers, enantiomers and salts thereof.

Compounds of the general formula (I) which have proved to be very particularly effective are those in which $R^1$ is

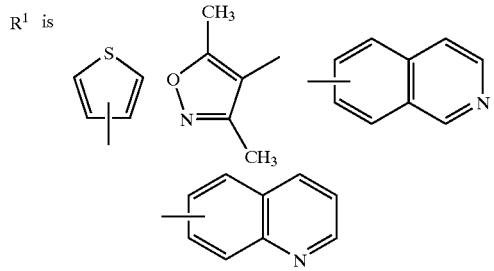

$R^2$ and $R^3$ are each, independently of one another, $C_1$–$C_6$-alkyl, or $R^2$ and $R^3$ together with the nitrogen atom form a $C_5$–$C_6$-cycloalkyl ring which may optionally be interrupted by a further nitrogen atom in the ring, where the $C_5$–$C_6$-cycloalkyl ring may optionally be substituted by $C_1$–$C_4$-alkyl, and $R^4$ is hydrogen, or is the group CF3, —O—$CH_3$ or nitro, and the isomers, diastereomers, enantiomers and salts thereof.

The compounds of the invention essentially increase the rate of arrangement of peroxynitrite into harmless products and can thus be used for producing a medicament for the treatment and prophylaxis of free radical-mediated cell damage.

It was possible to show by NMR and UV/VIS spectroscopy that the compounds of the invention catalyze the rearrangement of peroxynitrite into harmless final products, namely nitrate and nitrite. Peroxynitrite is a strong oxidizing agent which is produced by the reaction of nitric oxide (NO) and superoxide anion ($O_2^-$). It was possible to show that NO is generated in many cells such as, for example, in macrophages, in neutrophilic cells, hepatocytes and endothelial cells. The direct reaction of NO and $O_2$–results in the formation of peroxynitrite ion which rapidly breaks down under physiological conditions into oxidizing intermediates. These oxidizing intermediates are responsible for the damage to biological targets.

The results of this damage may be associated with pathological consequences including the oxidation and nitration of proteins, lipids and DNA. Peroxynitrite is able to cross cell membranes at a distinctly higher speed than other oxidizing agents, and peroxynitrite can penetrate rapidly into the interior of cells even in the presence of a biological membrane. Peroxynitrite is known to nitrate tyrosine residues in proteins, and it oxidizes sulfhydryl radicals, methionines and macromolecules such as, for example, metalloenzymes, DNA and lipids.

Because of its high reactivity, peroxynitrite has been thought to be connected with many disorders. The invention relates to the use of the compounds of the invention for producing a medicament for the treatment and prophylaxis of chronic and acute neurodegenerative disorders, autoimmune diseases, inflammatory disorders, infectious diseases, cancer, viral infections, cardiovascular disorders and nephrological disorders. By chronic neurodegenerative disorders are meant Huntington's disease, ALS (amyotrophic lateral sclerosis), Parkinson's disease, dementia such as, for example, Alzheimer's disease, HIV dementia and presenile dementia, Korksakoff's disease, epilepsy, schizophrenia, depression, and by acute neurodegenerative disorders are meant cerebral ischemia and neurotrauma, by autoimmune diseases and/or inflammatory disorders are meant hypotension, ARDS (adult respiratory distress syndrome), sepsis and septic shock, rheumatoid arthritis, osteoarthritis, inflammatory disease of the pelvis/bowel (bowel disease), meningitis, multiple sclerosis, alopecia and psoriasis, by infectious diseases are meant diseases caused by unicellular parasites, by cancer are meant solid tumors and leukemia, by viral infections are meant cytomegalovirus infections, hepatitis, hepatitis B and C and HIV disorders, by cardiovascular disorders are meant ischemic reperfusion disorder, stenoses, arterioscleroses and restenoses, and by nephrological disorders are meant glomerulonephritis.

For use of the compounds of the invention as medicaments, they are converted into the form of a pharmaceutical product which, besides the active ingredient, contains organic or inorganic inert pharmaceutical carrier materials which are suitable for enteral or parenteral administration, such as, for example, water, gelatin, gum arabic, lactose, starch, magnesium stearate, talc, vegetable oils, polyalkylene glycols etc. The pharmaceutical products may be in solid form, for example as tablets, coated tablets, suppositories, capsules or in liquid form, for example as solutions, suspensions or emulsions. They additionally contain where appropriate excipients such as preservatives, stabilizers, wetting agents or emulsifiers, salts to alter the osmotic pressure or buffers.

The present invention likewise relates to these pharmaceutical products.

The present invention likewise relates to the use of the compounds of the general formula I for producing a medicament for the treatment and prophylaxis of disorders which include chronic and acute neurodegenerative disorders, autoimmune diseases, inflammatory disorders, infectious diseases, cancer, viral infections, cardiovascular disorders and nephrological disorders.

By chronic neurodegenerative disorders are meant Huntington's disease, ALS (amyotrophic lateral sclerosis), Parkinson's disease, dementia such as, for example, Alzheimer's disease, HIV dementia and presenile dementia, Korksakoff's disease, epilepsy, schizophrenia, depression, and by acute neurodegenerative disorders are meant cerebral ischemia and neurotrauma, by autoimmune diseases and/or inflammatory disorders are meant hypotension, ARDS (adult respiratory distress syndrome), sepsis and septic shock, rheumatoid arthritis, osteoarthritis, inflammatory disease of the pelvis/bowel (bowel disease), meningitis, multiple sclerosis, alopecia and psoriasis, by infectious diseases are meant diseases caused by unicellular parasites, by cancer are meant solid tumors and leukemia, by viral infections are meant cytomegalovirus infections, hepatitis, hepatitis B and C and HIV disorders, by cardiovascular disorders are meant ischemic reperfusion disorder, stenoses, arteriosciereses and restenoses, and by nephrological disorders are meant glomerulonephritis.

Suitable for parenteral use are, in particular, solutions for injection or suspensions, especially aqueous solutions of the active compounds in polyethoxylated castor oil.

Surface-active excipients such as salts of bile acids or animal or vegetable phospholipids, but also mixtures thereof, and liposomes or constituents thereof can also be wed as carrier systems.

Suitable for oral use are, in particular, tablets, coated tablets or capsules with talc and/or carbohydrate carriers or binders such as, for example, lactose, corn starch or potato starch. Use is also possible in liquid form such as, for example, oral solution, to which a sweetener is added where appropriate.

The present invention likewise relates to the enteral, parenteral and oral administrations.

The dosage of the active ingredients may vary depending on the route of administration, age and weight of the patient, nature and severity of the disorder to be treated and similar factors. The daily dose is 0.5–1 000 mg, preferably 50–200 mg, it being possible to give the dose as a single dose to be administered on one occasion or divided into two or more daily doses.

The present invention likewise relates to medicaments for the treatment of the abovementioned disorders which comprise at least one compound of the general formula I and medicaments with suitable formulating substances and carriers.

The compounds of the invention of the general formula I are peroxynitrite rearrangement catalysts.

Where the preparation of the starting compounds is not described, they are known or can be prepared in analogy to known compounds or processes described herein. It is likewise possible to carry out all variations described herein in parallel reactors or using combinatorial techniques.

Mixtures of isomers can be fractionated into the enantiomers or E/Z isomers by conventional methods such as, for example, crystallization, chromatography or salt formation.

The salts are prepared in a conventional way by adding the equivalent amount or an excess of a base or acid, which is in solution where appropriate, to a solution of the compound of the formula I, and removing the precipitate or working up the solution in a conventional way.

PREPARATION OF THE COMPOUNDS OF THE INVENTION

The following examples illustrate the preparation of the compounds of the invention without restricting the scope of the claimed compounds to these examples.

The compounds of the invention of the general formula I can be prepared as shown in the following general process scheme:

Process scheme:

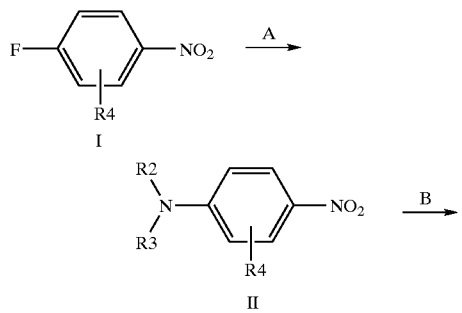

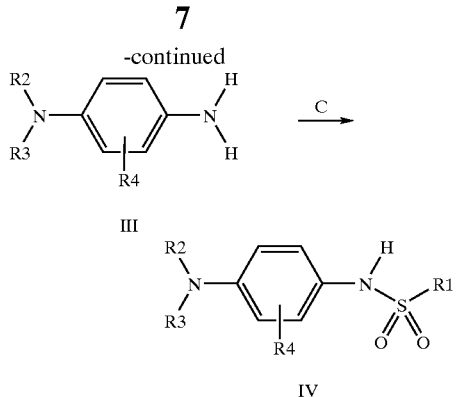

Starting from an optionally substituted fluoronitrobenzene of the general formula I, amine can be introduced by nucleophilic substitution of the fluorine. The aromatic nitro group in the position para to the introduced amine in compounds of type II can then be converted by hydrogenation into an aromatic amine of the general formula III. These amines can be converted by sulfonation with sulfonyl chlorides into the corresponding sulfonamides of the general formula IV, to which this application relates.

GENERAL REACTION METHODS

General Method A:

Introduction of the amine by nucleophilic substitution An optionally substituted fluoronitrobenzene is introduced into ethanol, and 3 equivalents of an amine are added dropwise while cooling in an ice bath. The mixture is then stirred at room temperature. If no reaction takes place, it is heated to 100° C. After the reaction is complete, 2N HCl is added to the reaction mixture and, after extraction with dichloromethane, washing, drying and concentration, are usually reacted without further purification.

General Method B:

Reduction of Nitro Groups

The compound to be reduced is dissolved in ethyl acetate, tetrahydrofuran, methanol or ethanol or mixtures of these solvents and hydrogenated over 2–5% (based on the nitro compound) of palladium on carbon (10%) under atmospheric pressure. After the hydrogen uptake ceases, the mixture is filtered with suction, the residue is washed with ethyl acetate, methanol or ethanol, and the filtrate is concentrated in vacuo. The crude product is usually reacted without further purification.

General Method C:

Sulfonation of an Aromatic Amine

The amine is dissolved in dichloromethane and, after addition of 1.1 equivalents of 4-dimethylaminopyridine (for larger batches the 4-dimethylaminopyridine is replaced by 1.1 equivalents of pyridine and a spatula tip of 4-dimethylaminopyridine) and 1.1 equivalents of a sulfonyl chloride, stirred at room temperature. After the reaction is complete, the reaction mixture is poured into water, extracted with dichloromethane or ethyl acetate, washed, dried and concentrated. Purification takes place by column chromatography.

EXEMPLARY EMBODIMENTS

Example 1

Preparation of 3,5-dimethylisoxazole-4-sulfonic acid 4-pyrrolidin-1-ylphenylamide Starting from 80 mg of 4-pyrrolidin-1-ylphenylamine and by reaction with 3,5-dimethylisoxazole-4-sulfonyl chloride, 140 mg of 3,5-dimethylisoxazole-4-sulfonic acid 4-pyrrolidin-1-ylphenylamide are prepared by general method C.

MS (EI) =321 (molecular ion peak)

Example 2

Preparation of 3,5-dimethylisoxazole-4-sulfonic acid 4-pyrrolidin-1-yl-2-trifluoromethylphenylamide Starting from 80 mg of 5-fluoro-2-nitrobenzotrifluoride and by reaction with pyrrolidine, 138 mg of 5-pyrrolidinyl-2-nitrobenzotrifluoride are prepared by general method A. The crude product is hydrogenated by general method B. 97 mg of 5-pyrrolidinyl-2-aminobenzo-trifluoride are obtained. Starting from this and by reaction with 3,5-dimethylisoxazole-4-sulfonyl chloride by general method C, 80 mg of 3,5-dimethylisoxazole-4-sulfonic acid 4-pyrrolidin-1-yl-2-trifluoromethyl-phenylamide are prepared.

MS (EI) =389 (molecular ion peak)

Example 3

Preparation of 3,5-dimethylisoxazole-4-sulfonic acid 4-piperidin-1-ylphenylamide Starting from 25 mg of 4-piperidinoaniline and by reaction with 3,5-dimethylisoxazole-4-sulfonyl chloride, 21 mg of 3,5-dimethylisoxazole-4-sulfonic acid 4-piperidin-1-ylphenylamide are prepared by general method C.

MS (EI) =335 (molecular ion peak)

Example 4

Preparation of quinoline-8-sulfonic acid 4-piperidin-1-ylphenylamide

Starting from 25 mg of 4-piperidinoaniline and by reaction with quinoline-8-sulfonyl chloride, 11 mg of quinoline-8-sulfonic acid 4-piperidin-1-ylphenylamide are prepared by general method C.

MS (EI) =367 (molecular ion peak)

Example 5

Preparation of thiophene-2-sulfonic acid 2-methoxy-4-pyrrolidin-1-ylphenylamide 3 g of 5-fluoro-2-nitrophenol are dissolved in DMF and, after addition of 1.1 equivalent each of iodomethane and cesium carbonate, stirred at room temperature. After the reaction is complete, the reaction mixture is poured into water, extracted with diethyl ether, washed and concentrated. 3.2 g of 2-methoxy-4-fluoronitro-benzene are produced. Starting from this, 4.2 g of 2-methoxy-4-pyrrolidinylnitrobenzene are prepared by reaction with pyrrolidine by general reaction method A. The crude product is hydrogenated by general method B. 3.6 g of 2-methoxy-4-pyrrolidinylaminobenzene are obtained. Starting from 150 mg of the crude product and by reaction with 2-thiophenesulfonyl chloride, 154 mg of thiophene-2-sulfonic acid 2-methoxy-4-pyrrolidin-1-ylphenylamide are prepared by general method C.

Example 6

Preparation of quinoline-8-sulfonic acid 4-pyrrolidin-1-ylphenylamide

Starting from 80 mg of 4-(1-pyrrolidinyl) and by reaction with quinoline-8-sulfonyl chloride, 45 mg of quinoline-8- sulfonic acid 4-pyrrolidin-1-ylphenylamide are prepared by general method C.

MS (EI) =353 (molecular ion peak)

Example 7

Preparation of thiophene-2-sulfonic acid 4-(4-methyl-piperazin-1-yl)phenylamide

Starting from 80 mg of 4-(4-methylpiperazino)aniline and by reaction with thiophene-2-sulfonyl chloride, 52 mg of thiophene-2-sulfonic acid 4-(4-methyl-piperazin-1-yl)phenylamide are prepared by general method C.

MS (EI) =337 (molecular ion peak)

Example 8

Preparation of thiophene-2-sulfonic acid 4-dimethyl-amino-2-nitrophenylamide

Starting from 100 mg of 4-amino-N,N-dimethyl-3-nitroaniline and by reaction with thiophene-2-sulfonyl chloride, 12 mg of thiophene-2-sulfonic acid 4-dimethylamino-2-nitrophenylamide are prepared by general method C.

MS (EI) =327 (molecular ion peak)

Example 9

Preparation of 3,5-dimethylisoxazole-4-sulfonic acid 4-dimethylamino-2-nitrophenylamide Starting from 100 mg of 4-amino-N,N-dimethyl-3-nitroaniline and by reaction with 3,5-dimethylisoxazole-4-sulfonyl chloride, 56 mg of 3,5-dimethylisoxazole-4-sulfonic acid 4-dimethylamino-2-nitrophenylamide are prepared by general method C.

MS (EI) =340 (molecular ion peak)

The invention further relates to pharmaceutical compositions comprising a compound of the general formula I in which $R^1$ is a $C_1$–$C_6$-alkyl or is a $C_5$–$C_6$-cycloalkyl which may optionally be substituted one or more times by $C_1$–$C_6$-alkyl and whose ring may optionally be interrupted by one or more nitrogen, sulfur or oxygen atoms and/or may contain one or more possible double bonds in the ring, or is a $C_3$–$C_7$-aryl or $C_3C_{12}$-heteroaryl, which may optionally be substituted one or more times, identically or differently, by halogen, hydroxyl, $C_1$–$C_6$-alkyl or $C_1$–$C_6$-alkoxy, $R^2$ and $R^3$ are each, independently of one another, $C_1$–$C_6$-alkyl or $C_1$–$C_6$-alkoxy, or $R^2$ and $R^3$ together with the nitrogen atom form a $C_5$–$C_6$-cycloalkyl ring which may optionally be interrupted by a further nitrogen atom in the ring, where the $C_5$–$C_6$-cycloalkyl ring may optionally be substituted by $C_1$–$C_4$-alkyl, and $R^4$ is hydrogen, hydroxyl, nitro, halogen, $C_1$–$C_6$-alkyl or the group COOH, $CF_3$ or $C_1$–$C_6$-alkoxy, and the isomers, diastereomers, enantiomers and salts thereof.

The compositions of the invention can be used for the treatment and prophylaxis of disorders which include chronic and acute neurodegenerative disorders, autoimmune diseases, inflammatory disorders, infectious diseases, cancer, viral infections, cardiovascular disorders and nephrological disorders.

By chronic neurodegenerative disorders are meant Huntington's disease, ALS (amyotrophic lateral sclerosis), Parkinson's disease, dementia such as, for example, Alzheimer's disease, HIV dementia and presenile dementia, Korksakoff's disease, epilepsy, schizophrenia, depression, and by acute neurodegenerative disorders are meant cerebral ischemia and neurotrauma, by autoimmune diseases and/or inflammatory disorders are meant hypotension, ARDS (adult respiratory distress syndrome), sepsis and septic shock, rheumatoid arthritis, osteoarthritis, inflammatory disease of the pelvis/bowel (bowel disease), meningitis, multiple sclerosis, alopecia and psoriasis, by infectious diseases are meant diseases caused by unicellular parasites, by cancer are meant solid tumors and leukemia, by viral infections are meant cytomegalovirus infections, hepatitis, hepatitis B and C and HIV disorders, by cardiovascular disorders are meant ischemic reperfusion disorder, stenoses, arterioscleroses and restenoses, and by nephrological disorders are meant glomerulonephritis.

DESCRIPTION OF THE FIGURE

FIG. 1 shows the time-dependent breakdown of peroxynitrite in the presence and absence of a catalyst administered in one-tenth the stoichiometric amount.

The following examples describe the biological effect of the compounds of the invention without restricting the invention to these examples.

Example 1

Measurement of the Kinetics of the Conversion of Peroxynitrite into Nitrate by UV Spectrometry The following are used: a UV spectrometer
a stopped flow device with slotted-on cuvette laboratory apparatus for volumetric work reagents (buffers, peroxynitrite solution, catalysts)

The peroxynitrite content of the concentrated peroxynitrite solution is determined. A molar extinction coefficient of $\epsilon=1\,670$ is used as basis. The solution is diluted with water to reach an absorption of about 1.6 at the observation wavelength of 301 nm. The pH of the stock solution produced in this way should not fall below 11.

A solution of the catalyst to be investigated is prepared in phosphate buffer appropriate for the peroxynitrite concentration set, in such a way that, taking account of the given conditions in the stopped flow device, the desired amounts of catalyst solution and peroxynitrite can be brought together for reaction. The buffer of the catalyst solution must have sufficient capacity for it to be possible for the peroxynitrite solution, which is still strongly alkaline, to be adjusted to, and maintained at, the desired pH. The catalysts are added in one-tenth the stoichiometric amount (FIG. 1).

The metering syringes of the stopped flow system are charged with the two solutions and used to charge the cuvette which is present in the UV spectrometer. The absorptions at 301 nm are measured simultaneously. The rearrangement of peroxynitrite to nitrate results in the decrease in the absorption, which assumes a constant value after some time. The rearrangement is complete at this time, and the data recording is stopped.

The measured data are analyzed, and the peroxynitrite concentration can be calculated from the characteristic kinetic data of the plot resulting therefrom. These data serve to characterize the catalyst to be investigated. In order to take account of the spontaneous decomposition of peroxynitrite, for each peroxynitrite preparation used initially the decomposition behavior of the peroxynitrite solution is found on addition of the buffer without catalyst content, and the relation between the characteristic data thereof and those obtained from a measurement with catalyst is found.

$$\text{Relative rate constant} = \frac{\text{Intrinsic decomposition of the peroxynitrite used at the described pH}}{\text{Catalyzed decomposition}} \quad (\text{FIG. 1})$$

Example 2

Oxidation of Dihydrorhodamine to Rhodamine

The concentration of peroxynitrite is determined by reaction with dihydrorhodamine (DHR) to give rhodamine. The rhodamine fluorescence emission is measured at 520 nm after excitation with light of a wavelength of 485 nm. Catalytic conversion of peroxynitrite by a test substance leads to a decrease in the peroxynitrite concentration and thus also to a decrease in the rhodamine fluorescence, because less DHR can be converted into rhodamine. The search for peroxynitrite-degrading catalysts is carried out at neutral pH. Peroxynitrite is stable for only a few seconds at neutral pH. It is therefore necessary for peroxynitrite to be kept alkaline until contacted with the test substance and DHR as detection reagent. The search for catalysts takes place by rapid mixing of the following components:

10 $\mu$l of 10 $\mu$M DHR;

100 $\mu$m diethylenetriaminepentaacetic acid in 75 mM Na phosphate buffer at pH 5.6

5 $\mu$l of peroxynitrite in 9 mM NaOH 0.75 $\mu$l test substance in 30% DMSO/H$_2$O The measurement takes place in a standard microtiter plate fluorescence measuring apparatus

Example 3

SIN-1 Damage Assay with Primary Neuronal Cultures from Neonatal Rat Cerebellum A primary culture of cells from neonatal rat cerebellum is set up for in vitro testing of substances for neuroprotection against damage induced by peroxy-nitrite. The measurement of cell death or survival of neurons in this culture takes place indirectly through a measurement of the conversion of the dye Alamar blue into its reduced fluorescent form. The peroxynitrite donor SIN-1 (3-morpholinosydnonimine) is used for the damage.

To obtain the cells, Wistar rats (P8) are sacrificed by decapitation, the cerebella are obtained, the meninges are removed from the cerebellum (HBSS (GIBCO, 14025-050) 4° C.), cut up and transferred into a 15 ml Falcon tube, the supernatant is aspirated off, and then the cerebella are trypsinized by adding 500 $\mu$l of trypsin/EDTA solution (GIBCO #2530-054)/cerebellum. After incubation (20 min, 37° C.), the trypsinized cerebella are washed 3× with 10 ml of HBSS. This is followed by tritration by addition of 500 $\mu$l of 0.05% strength DNAseI (BOEHRINGER MANNHEIM, #14953000) per cerebellum. Using a 5 ml pipette, then a flame-polished Pasteur pipette and finally (if necessary) a drawn-out flame-polished Pasteur pipette, the cells are isolated and mixed with 10 ml of complete medium (100 ml of Neurobasal (GIBCO #21103-049), 1 ml of B27 supplement (GIBCO #17504-044), 0.4 ml of pen/strep (10 000 IU/ml/10 000 UG/ml) (GIBCO #15140-160), 0.8 ml of KCl stock solution (MERCK, 1.04936.0500), 1 ml of L-glutamine (100×–200 mM) (GIBCO #15140-106). The isolated cells are then centrifuged (10 min at 600 rpm), washed 1× with complete medium and resuspended in 20 ml of complete medium, counted and diluted to 2×10$^6$ ml. 100 $\mu$l of complete medium are introduced into each well of a 96-well microtiter plate, and 100 $\mu$l of cell suspension are added (=day 1 in vitro). The microtiter plates are previously coated in the following way: 50 $\mu$l of poly-L-lysine (MW 70-105 kD) (SIGMA #P-6282) are applied to each well, and the plates are then incubated in an incubator for about 90 min. Before the cells are plated out, the solution is aspirated off again and washed 2× with HBSS and with sterile double-distilled water. 24 h after plating out, the cells are damaged by addition of SIN-1. Test substances are applied 1 h before addition of SIN-1 (single concentration of 10 or 30 $\mu$m, or as concentration series, CALBIOCHEM, 567028). Cell function is measured on day 2 (day2 in vitro) with Alamar blue (10 $\mu$l/well) (BIOSOURCE INT., DAL1100). Incubation for 3 hours is followed by measurement in a fluorescence reader (Victor, Wallac, extinction 544 nm/emission 590 nm). IC$_{50}$ values are calculated by the Excel plug-in XLfit.

Results of the examples are indicated in the following table:

| Example | Structure | Rate constant | DHR oxidation assay IC$_{50}$ [$\mu$M] | Cytotoxicity assay ED$_{50}$ [$\mu$M] |
|---|---|---|---|---|
| 1 | 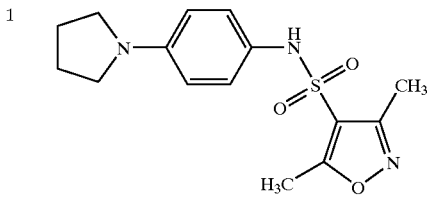 | 1.1 | 1.1 | 4.4 |

-continued

| Example | Structure | Rate constant | DHR oxidation assay IC$_{50}$ [μM] | Cytotoxicity assay ED$_{50}$ [μM] |
| --- | --- | --- | --- | --- |
| 2 | 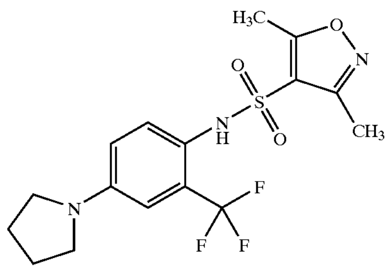 | 1.3 | 2.4 | 6.6 |
| 3 | 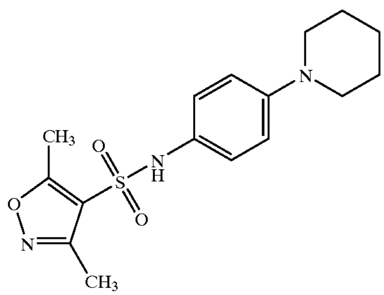 | 1.4 | 0.95 | 5.3 |
| 4 | 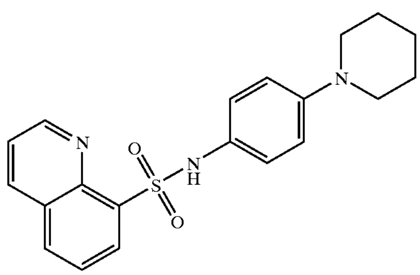 | 1.4 | 1.1 | 8.7 |
| 5 | 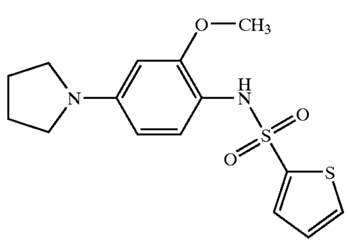 | 1.9 | 8.1 | 5.9 |
| 6 | 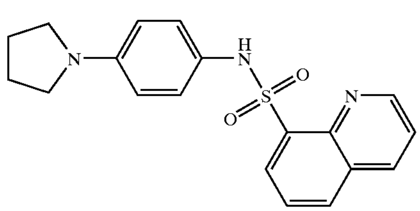 | 1.2 | 1.5 | 5.2 |
| 7 | 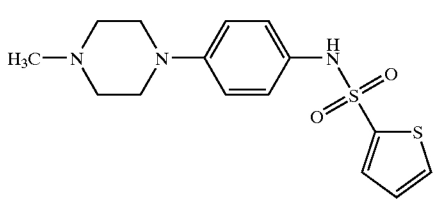 | 1.3 | 1.9 | 5.7 |

| Example | Structure | Rate constant | DHR oxidation assay IC$_{50}$ [μM] | Cytotoxicity assay ED$_{50}$ [μM] |
|---|---|---|---|---|
| 8 | 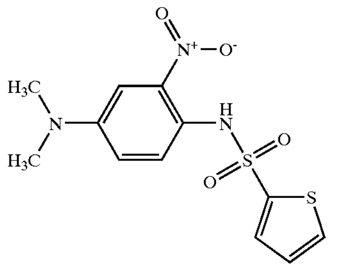 | 1.6 | 1.6 | 6.4 |
| 9 | 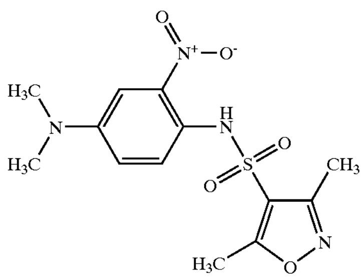 | 1.6 | 2 | 8.6 |
| Fe (III) T MPyP*) | 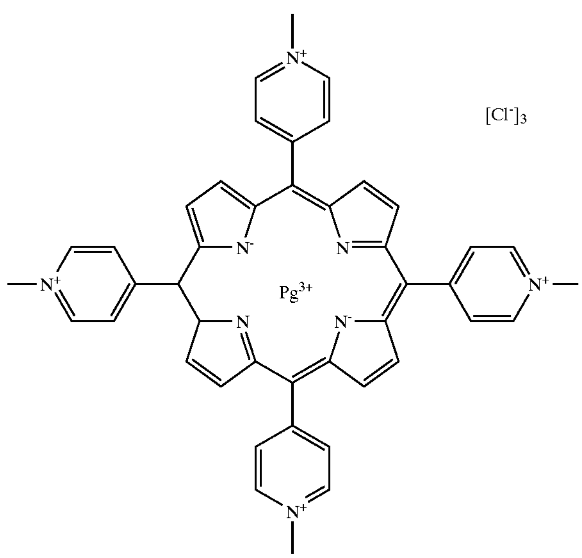 | 8.1 | | 2.2 |

*)added in 100th the stoichiometric amount

The compounds of the invention showed better properties compared with known metalloporphyrins, such as, for example, better brain penetration.

What is claimed is:

1. A compound of formula I

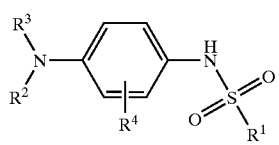

(I)

in which
$R^1$ is a $C_5$–$C_6$-alkylene-containing ring which may optionally be substituted one or more times by $C_1$–$C_6$-alkyl and which ring is interrupted by one or more nitrogen, sulfur or oxygen atoms and may contain one or more possible double bonds in the ring, or is a $C_3$–$C_{12}$-heteroaryl, which may optionally be substituted one or more times, identically or differently, by halogen, hydroxyl, $C_1$–$C_6$-alkyl or $C_1$–$C_6$-alkoxy, $R^2$ and $R^3$ form a $C_5$–$C_6$-alkylene-containing ring together with the nitrogen atom, which may optionally be substituted by $C_1$–$C_4$-alkyl, and $R^4$ is hydrogen, hydroxyl, nitro, halogen, $C_1$–$C_6$-alkyl, COOH, CF$_3$ or $C_1$–$C_6$-alkoxy, or an the isomer, diastereomer, enantiomer thereof, or a salt thereof, wherein the compound of formula I is not

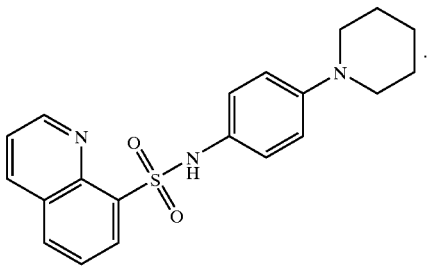

2. A compound of formula I according to claim 1, in which
   $R^1$ is a $C_5$–$C_6$-alkylene-containing ring which may optionally be substituted one or more times by methyl, and which ring is interrupted by one or more nitrogen, sulfur or oxygen atoms and one or more possible double bonds may be present in the ring, or is a $C_3$–$C_{12}$-heteroaryl,
   $R^2$ and $R^3$ form a $C_5$–$C_6$-alkylene-containing ring together with the nitrogen atom, which may optionally be substituted by $C_1$–$C_4$-alkyl, and
   $R^4$ is hydrogen, $CF_3$, —O—$CH_3$ or nitro,
   or an the isomer, diastereomer, enantiomer thereof, or a salt thereof.

3. A compound of formula I according to claim 1, in which
   $R^1$ is

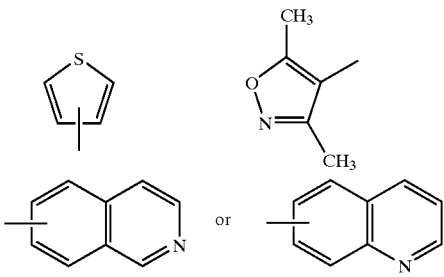

$R^2$ and $R^3$ form a $C_5$–$C_6$-alkylene-containing ring together with the nitrogen atom, which may optionally be substituted by $C_1$–$C_4$-alkyl, and
   $R^4$ is hydrogen, $CF_3$, —O—$CH_3$ or nitro,
   or an the isomer, diastereomer, enantiomer thereof, or a salt thereof.

4. A compound of formula I

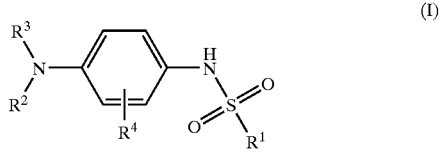

(I)

in which
   $R^1$ is a $C_5$–$C_6$-alkylene-containing ring which may optionally be substituted one or more times by $C_1$–$C_6$-alkyl and which ring is interrupted by one or more nitrogen, sulfur or oxygen atoms and may contain one or more possible double bonds in the ring, or is a $C_3$–$C_{12}$-heteroaryl, which may optionally be substituted one or more times, identically or differently, by halogen, hydroxyl, $C_1$–$C_6$-alkyl or $C_1$–$C_6$-alkoxy, wherein $R^1$ is not

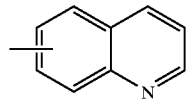

$R^2$ and $R^3$ form a $C_5$–$C_6$-alkylene-containing ring together with the nitrogen atom, which may optionally be substituted by $C_1$–$C_4$-alkyl, and
   $R^4$ is hydrogen, hydroxyl, nitro, halogen, $C_1$–$C_6$-alkyl, COOH, $CF_3$ or $C_1$–$C_6$-alkoxy,
   or an the isomer, diastereomer, enantiomer thereof, or a salt thereof.

5. A compound of formula I

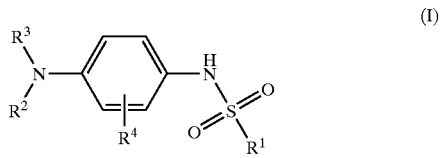

(I)

in which
   $R^1$ is a $C_5$–$C_6$-alkylene-containing ring which may optionally be substituted one or more times by $C_1$–$C_6$-alkyl and which ring is interrupted by one or more nitrogen, sulfur or oxygen atoms and may contain one or more possible double bonds in the ring, or is a $C_3$–$C_{12}$-heteroaryl, which may optionally be substituted one or more times, identically or differently, by halogen, hydroxyl, $C_1$–$C_6$-alkyl or $C_1$–$C_6$-alkoxy,
   $R^2$ and $R^3$ form a $C_5$-alkylene-containing ring together with the nitrogen atom, which may optionally be interrupted by a further nitrogen atom in the ring, and which may optionally be substituted by $C_1$–$C_4$-alkyl, and
   $R^4$ is hydrogen, hydroxyl, nitro, halogen, $C_1$–$C_6$-alkyl, COOH, $CF_3$ or $C_1$–$C_6$-alkoxy,
   or an the isomer, diastereomer, enantiomer thereof, or a salt thereof.

6. A compound of formula I

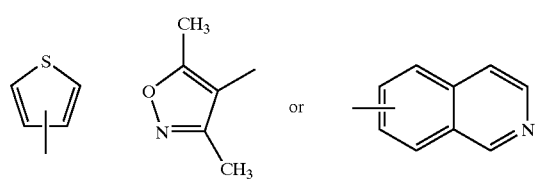

(I)

in which $R^1$ is

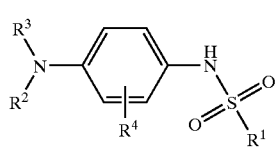

$R^2$ and $R^3$ form a $C_5$–$C_6$-alkylene-containing ring together with the nitrogen atom, which may optionally be interrupted by a further nitrogen atom in the ring, and which may optionally be substituted by $C_1$–$C_4$-alkyl, and $R_4$ is hydrogen, hydroxyl, nitro, halogen, $C_1$–$C_6$-alkyl, COON, $CF_3$ or $C_1$–$C_6$-alkoxy, or an the isomer, diastereomer, enantiomer thereof or a salt thereof.

7. A compound of formula I according to claim 6, wherein $R^1$ is

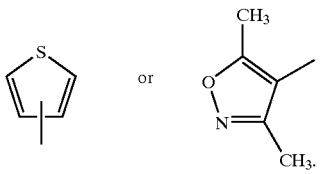

8. A compound of formula I according to claim 4, in which $R^1$ is a $C_5$–$C_6$-alkylene-containing ring which may optionally be substituted one or more times by methyl, and which ring is interrupted by one or more nitrogen, sulfur or oxygen atoms and one or more possible double bonds may be present in the ring, or is a or $C_3$–$C_{12}$-heteroaryl, $R^2$ and $R^3$ form a $C_5$–$C_6$-alkylene-containing ring together with the nitrogen atom, which may optionally be substituted by $C_1$–$C_4$-alkyl, and $R_4$ is hydrogen, $CF_3$, —O—$CH_3$ or nitro, or an the isomer, diastereomer, enantiomer thereof, or a salt thereof.

9. A compound of formula I according to claim 4, in which $R^1$ is

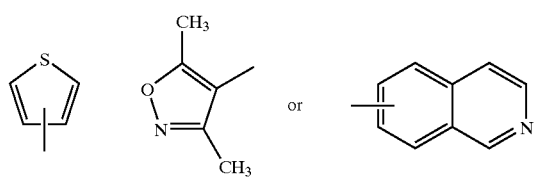

$R^2$ and $R^3$ form a $C_5$–$C_6$-alkylene-containing ring together with the nitrogen atom, which may optionally be substituted by $C_1$–$C_4$-alkyl, and $R_4$ is hydrogen, $CF_3$, —O—$CH_3$ or nitro, or an the isomer, diastereomer, enantiomer thereof, or a salt thereof.

10. A compound of formula I according to claim 5, in which $R^1$ is a $C_5$–$C_6$-alkylene-containing ring which may optionally be substituted one or more times by methyl, and which ring is interrupted by one or more nitrogen, sulfur or oxygen atoms and one or more possible double bonds may be present in the ring, or is a $C_3$–$C_{12}$-heteroaryl, $R^2$ and $R^3$ form a $C_5$-alkylene-containing ring together with the nitrogen atom, which may optionally be interrupted by a further nitrogen atom in the ring, and which may optionally be substituted by $C_1$–$C_4$-alkyl, and $R^4$ is hydrogen, $CF_3$, —O—$CH_3$ or nitro, or an the isomer, diastereomer, enantiomer thereof, or a salt thereof.

11. A compound of formula I according to claim 5, in which $R^1$ is

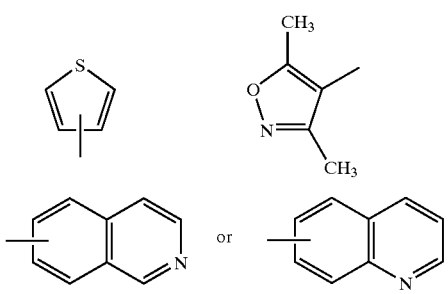

$R^2$ and $R^3$ form a $C_5$-alkylene-containing ring together with the nitrogen atom, which may optionally be interrupted by a further nitrogen atom in the ring, and which may optionally be substituted by $C_1$–$C_4$-alkyl, and $R^4$ is hydrogen, $CF_3$, —O—$CH_3$ or nitro, or an the isomer, diastereomer, enantiomer thereof, or a salt thereof 12. A compound of formula I according to claim 6, in which $R^2$ and $R^3$ form a $C_5$–$C_6$-alkylene-containing ring together with the nitrogen atom, which may optionally be interrupted by a further nitrogen atom in the ring, which may optionally be substituted by $C_1$–$C_4$-alkyl, and $R^4$ is hydrogen, $CF_3$, —O—$CH_3$ or nitro, or an the isomer, diastereomer, enantiomer thereof, or a salt thereof.

13. A compound, which is 3,5-dimethylisoxazole-4-sulfonic acid 4-pyrrolidin-1-ylphenylamide; 3,5-dimethylisoxazole-4-sulfonic acid 4-pyrrolidin-1-yl-2-trifluoromethylphenylamide; 3,5-dimethylisoxazole-4-sulfonic acid 4-piperidin-1-ylphenylamide; thiophene-2-sulfonic acid 2-methoxy-4-pyrrolidin-1-ylphenylamide; or thiophene-2-sulfonic acid 4-(4-methylpiperazin-1-yl)phenylamide.

14. A pharmaceutical composition comprising a pharmaceutically acceptable carrier and quinoline-8-sulfonic acid 4-pyrrolidin-1-ylphenylamide.

15. A pharmaceutical composition comprising a pharmaceutically acceptable carrier and a compound of claim 1.

16. A pharmaceutical composition comprising a pharmaceutically acceptable carrier and a compound of claim 4.

17. A pharmaceutical composition comprising a pharmaceutically acceptable carrier and a compound of claim 5.

18. A pharmaceutical composition comprising a pharmaceutically acceptable carrier and a compound of claim 6.

19. A method of treating Alzheimer's disease comprising administering to a patient in need thereof an effective amount of a pharmaceutical composition according to claim 15.

20. A method of treating Alzheimer's disease comprising administering to a patient in need thereof an effective amount of a pharmaceutical composition according to claim 16.

21. A method of treating Alzheimer's disease comprising administering to a patient in need thereof an effective amount of a pharmaceutical composition according to claim 17.

22. A method of treating Alzheimer's disease comprising administering to a patient in need thereof an effective amount of a pharmaceutical composition according to claim 18.

23. A method of treating Alzheimer's disease comprising administering to a patient in need thereof an effective amount of a pharmaceutical composition according to claim 14.

* * * * *